(12) United States Patent
Willimann

(10) Patent No.: US 10,307,452 B2
(45) Date of Patent: *Jun. 4, 2019

(54) ANTIMICROBIAL AND ANTIVIRAL COMPOSITION

(71) Applicant: Global Life Technologies Corp., Bethesda, MD (US)

(72) Inventor: John A. Willimann, Bethesda, MD (US)

(73) Assignee: GLOBAL LIFE TECHNOLOGIES CORP., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/953,688

(22) Filed: Apr. 16, 2018

(65) Prior Publication Data

US 2018/0236019 A1    Aug. 23, 2018

Related U.S. Application Data

(60) Continuation-in-part of application No. 15/285,714, filed on Oct. 5, 2016, now Pat. No. 9,943,561, which is a continuation-in-part of application No. 14/677,681, filed on Apr. 2, 2015, now Pat. No. 9,463,212, which is a continuation-in-part of application No. 14/318,972, filed on Jun. 30, 2014, now Pat. No. 8,999,406, which is a continuation-in-part of application No. 13/447,912, filed on Apr. 16, 2012, now Pat. No. 8,778,415, which is a continuation of application No. 12/658,116, filed on Feb. 1, 2010, now Pat. No. 8,158,163, which is a division of application No. 11/906,640, filed on Oct. 3, 2007, now abandoned, which is a continuation-in-part of application No. 11/189,242, filed on Jul. 26, 2005, now abandoned.

(51) Int. Cl.

| | | |
|---|---|---|
| *A61K 36/00* | (2006.01) |
| *A61K 36/48* | (2006.01) |
| *A61K 31/20* | (2006.01) |
| *A61K 33/40* | (2006.01) |
| *A61K 35/12* | (2015.01) |
| *A61K 36/752* | (2006.01) |
| *A61K 36/889* | (2006.01) |
| *A61K 31/045* | (2006.01) |
| *A61K 31/14* | (2006.01) |
| *A61K 36/886* | (2006.01) |
| *A61K 31/015* | (2006.01) |
| *A61K 36/9068* | (2006.01) |
| *A61K 36/185* | (2006.01) |
| *A61K 36/53* | (2006.01) |
| *A61K 36/534* | (2006.01) |

(52) U.S. Cl.
CPC ............ *A61K 36/48* (2013.01); *A61K 31/015* (2013.01); *A61K 31/045* (2013.01); *A61K 31/14* (2013.01); *A61K 31/20* (2013.01); *A61K 33/40* (2013.01); *A61K 35/12* (2013.01); *A61K 36/185* (2013.01); *A61K 36/53* (2013.01); *A61K 36/534* (2013.01); *A61K 36/752* (2013.01); *A61K 36/886* (2013.01); *A61K 36/889* (2013.01); *A61K 36/9068* (2013.01); *A61K 2300/00* (2013.01)

(58) Field of Classification Search
CPC ...................................................... A61K 36/00
USPC ........................................................ 424/725
See application file for complete search history.

(56) References Cited

U.S. PATENT DOCUMENTS 6,258,823 B1 *   7/2001   Holt ..................... C07D 498/16
                                                                514/291

* cited by examiner

*Primary Examiner* — Michael V Meller
(74) *Attorney, Agent, or Firm* — Robert M. Downey, P.A.

(57) ABSTRACT

A method of reducing the number of microorganisms entering the nose and proliferating in the nasal cavity including application of a solution of an antimicrobial, antiviral and antifungal composition to the anterior vestibular region of the nares. The antimicrobial, antiviral and antifungal solution includes ethyl alcohol as an active ingredient. Various embodiments may also include one or more of the following additional ingredients: orange oil; lemon oil; grapefruit oil; tangerine oil; mandarin oil; lime oil; bergamot oil; petitgrain essential oil; and other citrus oils; meadowfoam seed oil; soy oil; emu oil; grapefruit seed extract; glycine soja; simmondsia chinensis (Jojoba); lauric acid; chlorhexidine gluconate; ginger oil; lavender oil; peppermint oil; spearmint oil; aloe oil; one or more terpenes and/or terpenoids; and a preservative, such as benzalkonium chloride and vitamin E.

1 Claim, 4 Drawing Sheets

ANTIMICROBIAL AND ANTIVIRAL COMPOSITION

This patent application is a Continuation-In-Part (CIP) of patent application Ser. No. 15/285,714 filed on Oct. 5, 2016, which is a Continuation-In-Part (CIP) of patent application Ser. No. 14/677,681 filed on Apr. 2, 2015, which is a Continuation-In-Part (CIP) of patent application Ser. No. 14/318,972 filed on Jun. 30, 2014, which is a Continuation-In-Part (CIP) of patent application Ser. No. 13/447,912 filed on Apr. 16, 2012, which is a continuation patent application of patent application Ser. No. 12/658,116 filed on Feb. 1, 2010, which is a divisional of patent application Ser. No. 11/906,640 filed on Oct. 3, 2007, now abandoned, which is a Continuation-In-Part (CIP) patent application of patent application Ser. No. 11/189,242 filed on Jul. 26, 2005, now abandoned.

BACKGROUND OF THE INVENTION

Field of the Invention

This invention relates to antiseptic compositions and, more particularly, to a nasal antiseptic barrier composition having antimicrobial, antiviral, and antifungal properties.

Discussion of the Related Art

In recent years, outbreaks of new and potentially deadly diseases such as Middle East Respiratory Syndrome (MERS) and the Avian and Swine Influenzas have captured worldwide attention and concern. New and unusual strains of the flu virus have also emerged in the last few years and have spread throughout the world population at epidemic levels. It is believed that increases in world population, rapid travel between distance regions and high concentration of individuals in confined areas where there is poor air filtration (e.g. aircraft, trains, buses and tourist sites) have resulted in the increase in the number of, as well as mutation of, pathogenic organisms.

The onset of respiratory disease is primarily a result of inhalation of airborne pathogens through the nose and mouth. However, the oral cavity is better equipped to kill airborne pathogens before they can enter and infect the body. Specifically, saliva in the mouth captures many airborne pathogens before they are inhaled into the lungs. Once the saliva containing the pathogens is swallowed, stomach acids are highly effective in killing these pathogens before they can infect the body. The nasal passages, on the other hand, are less effective in trapping and killing microorganisms. Airborne pathogens inhaled through the nose usually enter the lungs where there can cause respiratory infection or other types of infection once these pathogens enter the blood stream.

Worldwide concern of epidemic outbreaks has lead to more drastic preventative measures including emergency mass production of new vaccines. Individuals have adopted preventive practices such as frequent hand washing and use of antiseptic hand lotions and wipes. While these are good practices to help reduce the possibility of infection, they are not long lasting and are usually only effective to kill germs that were on the hands or other areas of the body prior to cleansing. With little to no residual effect, the hands can become contaminated with pathogens shortly after washing.

Some societies have begun to use face masks as a means of protection against respiratory infections. Face masks are effective to prevent entry of pathogens into the respiratory system. However, the use of face masks is generally impractical, inefficient and socially unappealing.

Besides the concern for the health and well beings of individuals there are economic interests in preventing the spread on communicable diseases. For instance, over the course of just one year Americans suffer approximately 1 billion colds. The economic impact of the common cold is enormous. The National Center for Health Statistics (NCHS) estimates that over 70 million cases of the common cold in the United States required medical attention or resulted in restricted activities. Colds cause more than 50 million days of restricted activity and 25 million days lost from school and the work place. Overall, the estimated cost to the U.S. economy of the common cold and other related illnesses is approximately $150 billion per year.

Accordingly, there is an immediate need for more effective protection measures to decrease the spread of disease, and particularly respiratory infections that result from exposure to airborne pathogens.

SUMMARY OF THE INVENTION

The present invention is directed to an antimicrobial and antifungal barrier composition for topical application to the proximal anterior nares (rim surrounding the nostrils). The composition includes an antiseptic solution in combination with one or more citrus oils such as, for example, citrus sinensis (orange oil), lemon oil, grapefruit oil, tangerine oil, mandarin oil, lime oil, bergamot oil, and petitgrain essential oil. Examples of an antiseptic solution include one or more alcohols, such as ethyl alcohol, or hydrogen peroxide. The composition may further include one or more terpenes and/or terpenoids. The composition may include one or more additional ingredients, including: lauric acid; simmondsia chinensis (Jojoba); d-limonene; soy oil; emu oil; grapefruit seed extract; glycine soja; chlorhexidine gluconate; ginger oil; lavender oil; peppermint oil; spearmint oil; meadowfoam seed oil; aloe oil; and a preservative, such as sodium benzoate, benzalkonium chloride, BHT and vitamin E.

When properly applied to the skin surrounding the nostril openings, the composition has been proven effective in killing 99.99999% (7 log) or greater germs. This extremely efficient antimicrobial efficiency persists for at least 8 hours. Results from laboratory studies have shown efficacy in killing *streptococcus* (pneumoniae and pyogenes), *staphylococcus aureus, mycobacterium smegmatis*, and *haemophilus influenza* bacterias. The antimicrobial and antiviral composition of the present invention was further shown to be effective in eradicating the rhinovirus and influenza A virus (avian flu), as well as the corona virus. The corona virus is known to be the cause of SARS.

In addition to the anti-pathogen properties, the composition of the present invention has also been proven to help alleviate the body's immuno-response to many allergens including, but not limited to, dust mites, pollen, hay fever, animal dander, dust, particulate pollution, ozone, sulfur dioxide, and nitrogen oxide. The composition is effective in trapping these allergens and alleviating the body's response to their presence. In the case of ozone, SO2 and NO, the composition acts as a barrier in the nose and lessens the IGA response in the body. It is also believed that the composition works to lessen the Interleukin expression in the nose, especially ILB, commonly perspective for the inflammation response in the nasal cavity. A particularly effective formulation includes one or more of the following ingredients in combination with citrus oils, cocos nucifera and glycine soja: beeswax; bees milk; and fruit wax.

Objects and Advantages of the Invention

Considering the forgoing, it is a primary object of the present invention to provide an antimicrobial and antiviral composition for topical application to the anterior nostril openings for protecting against harmful exposure to airborne pathogens.

It is a further object of the present invention to provide a safe and highly effective antimicrobial and antiviral composition for topical application to the rim of each nostril to provide protection against a broad spectrum of harmful pathogens for at least 8 hours.

It is still a further object of the present invention to provide an antimicrobial and antiviral composition for topical application to the rim of each nostril to enhance the natural filtration properties of the nose.

It is yet a further object of the present invention to provide an antimicrobial and antiviral composition for topical application to the rim of the nostrils for trapping and killing airborne pathogens before these pathogens can replicate within the nasal cavity.

It is still a further object of the present invention to provide an antimicrobial and antiviral composition that significantly reduces the number of harmful pathogens that proliferate freely within the nasal cavity, thereby minimizing the degree and severity of potential respiratory infection.

It is still a further object of the present invention to provide an antimicrobial and antiviral composition of topical application to the rim of the nostrils, and wherein the composition has a pleasant scent and contributes to the lubrication and filtration of the nasal passages.

It is yet a further object of the present invention to provide an antimicrobial and antiviral composition for topical application to the rim of the nostrils, wherein the composition is effective in trapping allergens and alleviating the body's response to their presence.

These and other objects of the present invention are more readily apparent with reference to the detailed description which follows.

DETAILED DESCRIPTION OF THE PREFERRED EMBODIMENTS

Figure 1:
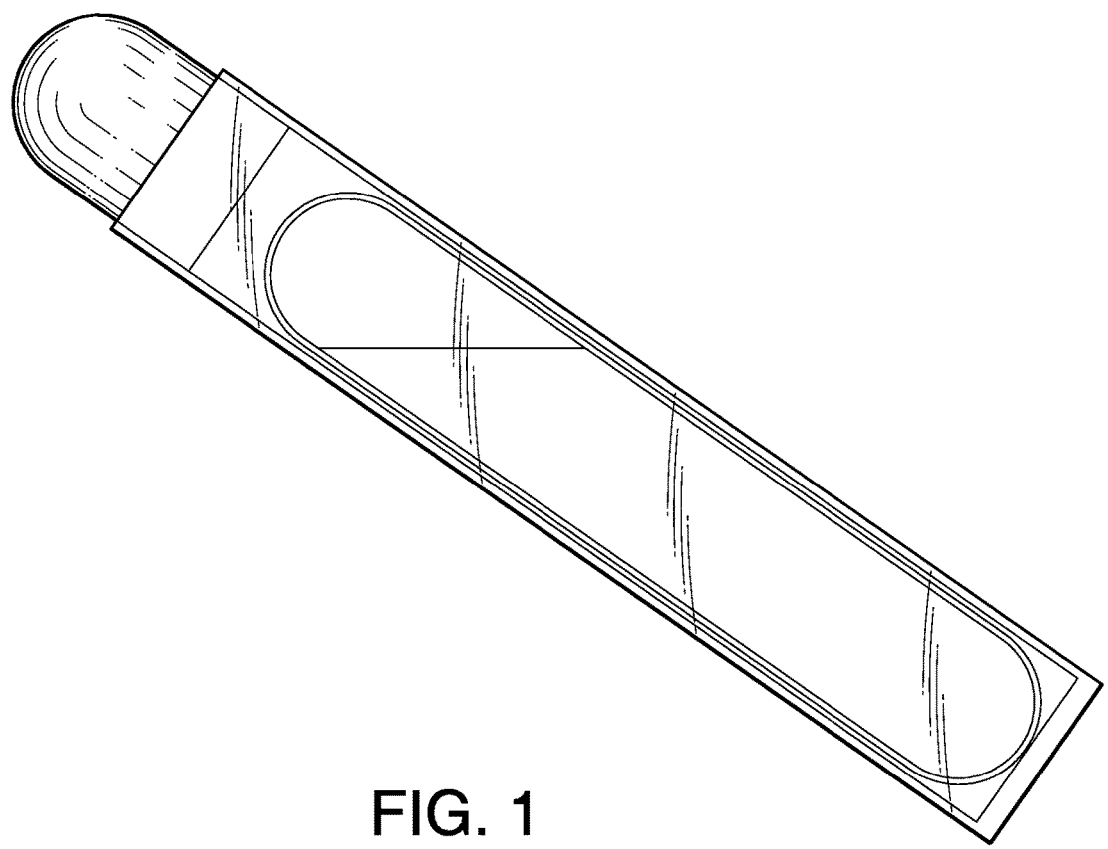
FIG. 1 is a side elevational view showing an applicator device in the prior art that has a glass ampoule contained within a flexible tube with a porous polyethylene applicator tip.

The present invention is directed to a long lasting antimicrobial and antiviral barrier composition for topical application to the proximal anterior nares (skin surface surrounding the opening of the nostrils). The antimicrobial and antiviral composition of the present invention incorporates the use of one or more antiseptic solutions in combination with one or more citrus oils and simmondsia chinensis (Jojoba). In one preferred embodiment, the antiseptic solution is USP ethyl alcohol. In another preferred embodiment, the antiseptic solution is hydrogen peroxide. Other alcohols and antiseptic agents are contemplated for use in the composition as the antiseptic solution, either alone or as a combination.

The essential ingredients of the composition are present according to the following percentages by weight of the composition:

| Essential Ingredients | Amount (% by Weight of the Composition) |
| --- | --- |
| Antiseptic solution | between 50% and 75% |

The antimicrobial and antiviral composition of the present invention may further include the following additional ingredients, alone or in combination: one or more terpenes and/or terpenoids; lauric acid; simmondsia chinensis; d-limonene; citrus oil (e.g., orange oil, lemon oil, grapefruit oil, tangerine oil, mandarin oil, lime oil, bergamot oil, and petitgrain essential oil); meadowfoam seed oil; soy oil; emu oil; grapefruit seed extract; glycine soja; chlorhexidine gluconate; ginger oil; lavender oil; peppermint oil; spearmint oil; aloe oil; and a preservative such as sodium benzoate, benzalkonium chloride, BHT, vitamin E. These additional ingredients of the composition may be present according to the following percentages by weight of the composition:

| Additional Ingredients | Amount (% by Weight of the Composition) |
| --- | --- |
| Laurie acid | between 0.05% and 49.90% |
| Citrus oil | between 0.05% and 49.90% |
| Simmondsia Chinensis | between 0.1% and 75% |
| D-limonene | between 0.01% and 5% |
| Glycine Soja (soy oil) | between 0.1% and 80% |
| Meadowfoam seed oil | between 0.1% and 60% |
| Emu oil | between 0.1% and 10% |
| Grapefruit Seed extract | between 0.1% and 8% |
| Aloe oil | between 0.1% and 30% |
| Benzalkonium Chloride | between 0.05% and 0.15% |
| Vitamin E | between 0.1% and 4% |
| Chlorhexidine Gluconate; | between 0.1% and 5% |
| Ginger oil | between 0.1% and 10% |
| Lavender oil | between 0.1% and 10% |
| Peppermint oil | between 0.1% and 10% |
| Spearmint oil | between 0.1% and 10% |
| Terpenes and/or terpenoids | between 0.05% and 10% |

A further embodiment of the composition has been proven to help alleviate the body's immune-response to many allergens and pollutants. The following ingredients have been found to be effective in the composition when present according to the following percentages by weight of the composition:

| Ingredients | Amount (% by Weight of the Composition) |
| --- | --- |
| Beeswax | between 0.01% and 30% |
| Bees Milk | between 0.01% and 30% |
| Fruit Wax | between 0.1% and 5% |

-continued

| Ingredients | Amount (% by Weight of the Composition) |
|---|---|

Antiseptic solutions such as ethyl alcohol and hydrogen peroxide typically evaporate at a rapid rate. For this reason, when antiseptic solutions are used alone, they usually have little to no residual effect. The base oils of the composition, namely one or more citrus oils and simmondsia chinensis, are effective to trap the antiseptic solution in a pseudo-emulsion antiseptic that remains active for an extended period of time. This allows the composition to have a long lasting antimicrobial and antiviral protection. The base oils also provide antimicrobial, antiviral and antifungal properties.

When the base oils are combined with the antiseptic solution, a synergistic effect is observed. For instance, the efficacy of any one of the base oils or the antiseptic solution, alone, does not exceed 99.99% (4 log). However, when all ingredients are combined in suitable ratios an unexpected removal efficiency rating (efficacy) of 99.99999% (7 log) or greater is achieved. This synergism is a key to the novelty of the composition, providing antimicrobial and antiviral kill levels that are significantly greater than those observed in connection with any of the ingredients individually or other known antimicrobials and antivirals.

The following examples demonstrate various combinations of ingredients, which have been observed to yield antimicrobial and antiviral kill rates of 7 log or greater.

Example 1

| Ingredient | Amount (% by Weight of the Composition) |
|---|---|
| USP Ethyl Alcohol (190 proof) | 62% |
| Citrus oil* | 8% |
| Simmondsia Chinensis | 28% |
| Lauric Acid | 0.9% |
| Benzalkonium Chloride | 0.1% |

Example 2

| Ingredient | Amount (% by Weight of the Composition) |
|---|---|
| USP Ethyl Alcohol (190 proof) | 54.8% |
| Citrus oil* | 2% |
| Aloe oil | 3% |
| Lauric Acid | 0.1% |
| Glycine Soja | 37% |
| Sodium Benzoate (preservative) | 0.1% |
| Meadowfoam seed oil | 2.0% |
| Terpenes and/or terpenoids | 1.0% |

Example 3

| Ingredient | Amount (% by Weight of the Composition) |
|---|---|
| USP Ethyl Alcohol (190 proof) | 54.8% |
| Citrus oil* | 5% |
| Aloe oil | 30% |
| Lauric Acid | 0.1% |
| Glycine Soja | 0.1% |

Example 4

| Ingredient | Amount (% by Weight of the Composition) |
|---|---|
| USP Ethyl Alcohol (190 proof) | 54.9% |
| Citrus oil* | 8% |
| Aloe oil | 14.45% |
| Lauric Acid | 0.2% |
| Glycine Soja | 14.45% |

Example 5

| Ingredient | Amount (% by Weight of the Composition) |
|---|---|
| USP Ethyl Alcohol (190 proof) | 54.9% |
| Emu Oil | 3% |
| Citrus oil* | 2% |
| Glycine Soja | 40% |
| Sodium Benzoate (preservative) | 0.1% |

Example 6

| Ingredient | Amount (% by Weight of the Composition) |
|---|---|
| USP Ethyl Alcohol (190 proof) | 50% |
| Citrus oil* | 2% |
| Simmondsia chinensis | 35% |
| Glycine Soja | 9.5% |
| Sodium Benzoate (preservative) | 0.1% |
| Benzalkonium chloride | 0.1% |
| Vitamin E | 0.3% |

Example 7

| Ingredient | Amount (% by Weight of the Composition) |
| --- | --- |
| USP Ethyl Alcohol (190 proof) | 65% |
| Citrus oil* | 2% |
| Simmondsia chinensis | 25% |
| Glycine Soja | 4.6% |
| Benzalkonium chloride | 0.1% |
| Vitamin E | 0.3% |

Example 8

| Ingredient | Amount (% by Weight of the Composition) |
| --- | --- |
| USP Ethyl Alcohol (190 proof) | 75% |
| Citrus oil* | 3% |
| Simmondsia chinensis | 17% |
| Glycine Soja | 2.5% |
| Benzalkonium chloride | 0.1% |
| Vitamin E | 0.4% |

Example 9

| Ingredient | Amount (% by Weight of the Composition) |
| --- | --- |
| USP Ethyl Alcohol (190 proof) | 62% |
| Citrus oil* | 5% |
| Simmondsia chinensis | 25% |
| Lavender Oil | 1% |
| Ginger Oil | 1.5% |
| Spearmint Oil | 2% |
| Peppermint Oil | 1% |
| Benzalkonium chloride | 0.1% |
| Vitamin E | 0.4% |

Example 10

| Ingredient | Amount (% by Weight of the Composition) |
| --- | --- |
| USP Ethyl Alcohol (190 proof) | 70% |
| Chlorhexidine Gluconate | 2% |
| Citrus oil* | 5% |

-continued

| Ingredient | Amount (% by Weight of the Composition) |
| --- | --- |
| Simmondsia chinensis | 17% |
| Lavender Oil | 1% |
| Ginger Oil | 1.5% |
| Spearmint Oil | 2% |
| Peppermint Oil | 1% |
| Benzalkonium chloride | 0.1% |
| Vitamin E | 0.4% |

*Citrus oil in the above examples may include one or more of the following: orange oil, lemon oil, grapefruit oil, tangerine oil, mandarin oil, lime oil, bergamot oil, and petitgrain essential oil.

In use, the antimicrobial and antiviral composition is applied to the skin surface surrounding the opening of the nostrils according to the following instructions:

1) Shake the bottle, container, applicator device or other vessel containing the composition well to insure complete mixture of the ingredients.

2) Apply between approximately 2-6 drops of the composition to the applicator member of the device being used for application.

3) Prepare to apply the composition to the rim of each nostril just past the nasal opening. Caution: Do not extend the applicator member into the nasal canal any further than 1.25 cm.

4) Carefully place only the applicator member just inside of the nostril opening. Using a gentle motion, make 3 or 4 circles to fully apply the composition to the rim of the nostril. Repeat this step for the other nostril.

5) Discard the applicator device if appropriate. Gently squeeze the nostrils together to ensure even distribution of the solution about the rim surrounding each nostril opening.

Figure 2:
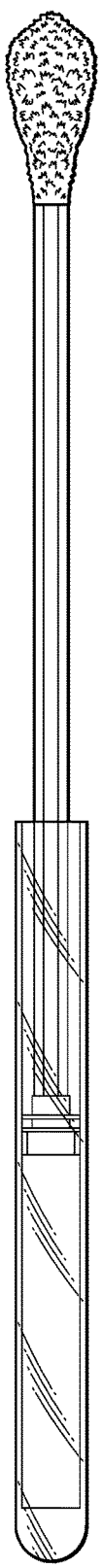
FIG. 2 is an elevational view of another applicator device in the prior art that includes a lower reservoir, a plunger on the end of a hollow tube and an applicator tip at the opposite end of the hollow tube.
Figure 3:
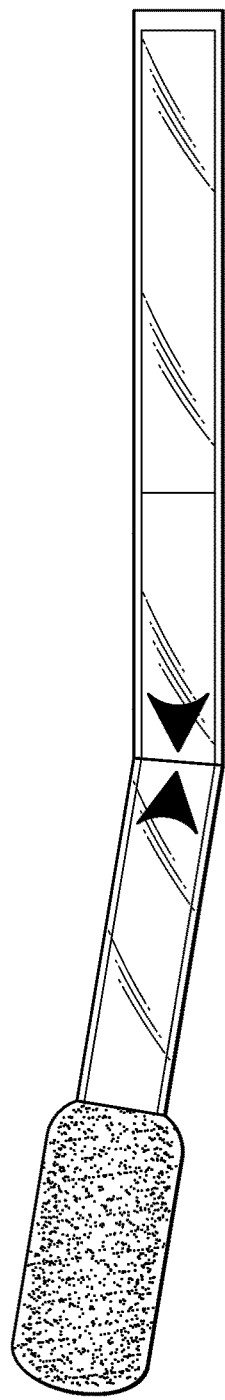
FIG. 3 is an elevational view of yet another type of applicator in the prior art having a hollow stem that is divided into two chambers by an internal breakable membrane and a cotton applicator tip at one end of the stem.
Figure 4:
FIG. 4 is an elevational view of yet another type of applicator in the prior art directed to a flocked swab having a polystyrene handle with a flock applicator tip.

It is noted that the applicator used for applying the antimicrobial and antiviral composition of the present invention can be any suitable applicator including, but not limited to those applicators shown in FIGS. 1-4 of the drawings or even the tip of a person's finger.

While the composition of the present invention has been described and exemplified according to several preferred embodiments thereof, it is recognized that departures from the instant disclosure are fully contemplated within the spirit and scope of the invention which is not to be limited except as defined in the following claims as interpreted under the Doctrine of Equivalents.

What is claimed is:

1. A method of reducing the number of microorganisms entering the nose and proliferating in the nasal cavity of a human in need thereof consisting essentially of administering to said human's nose a porous tip with a composition consisting essentially of ethanol and at least one component selected from the group consisting of orange oil, lemon oil, grapefruit oil, tangerine oil, mandarin oil, lime oil, bergamot oil, petitgrain oil, meadowfoam seed oil, jojoba oil, vitamin E, benzalkonium chloride, lauric acid, chlorhexidine gluconate, ginger oil, lavender oil, peppermint oil, spearmint oil, aloe oil, and terpenes, wherein said number of microorganisms are reduced from entering the nose and proliferating in the nasal cavity of a human in need thereof.

* * * * *